United States Patent [19]

de Loos-Vollebregt et al.

[11] Patent Number: 4,895,443

[45] Date of Patent: Jan. 23, 1990

[54] METHOD AND APPARATUS FOR ELECTROTHERMAL ATOMIZATION OF SAMPLES

[75] Inventors: Margaretha T. C. de Loos-Vollebregt, Pynacker; Leo de Galan, EM Schiedam, both of Netherlands

[73] Assignee: The Perkin-Elmer Corporation, Norwalk, Conn.

[21] Appl. No.: 208,936

[22] Filed: Jun. 20, 1988

[30] Foreign Application Priority Data

Jun. 19, 1987 [DE]  Fed. Rep. of Germany ....... 3720289

[51] Int. Cl.$^4$ ............................................. G01N 21/74
[52] U.S. Cl. ...................................... 356/36; 356/312
[58] Field of Search .................. 356/36, 311, 312, 244

[56] References Cited

U.S. PATENT DOCUMENTS 4,147,434  4/1979  Huber ................................ 356/36 X
4,361,401  11/1982  Smith, Jr. et al. .............. 356/312 X Primary Examiner—Vincent P. McGraw
Attorney, Agent, or Firm—Thomas P. Murphy; Edwin T. Grimes

[57] ABSTRACT

Sample introduction for atomic absorption spectrophotometry is effected by passage through a heated, axially displaceable capillary tube of a thermospray device; at least a fraction thereof is vaporized so that it emerges from one end of the capillary tube as a jet. A carrier liquid is forced through the capillary tube by a high pressure pump. In a retracted position, the outlet end of the capillary tube is disposed in a vacuum exhaust chamber. The sample is contained in a sample loop adapted to be connected into the flow path of the carrier liquid through an inlet valve. The capillary tube then advces so that said end is projected into a furnace pre-heated to drying temperature. The sample is thus deposited on the inner wall of the furnace whereas the vaporized carrier is drawn off. The furnace is then heated to atomization temperature and subsequently cooled to the drying temperature.

10 Claims, 8 Drawing Sheets

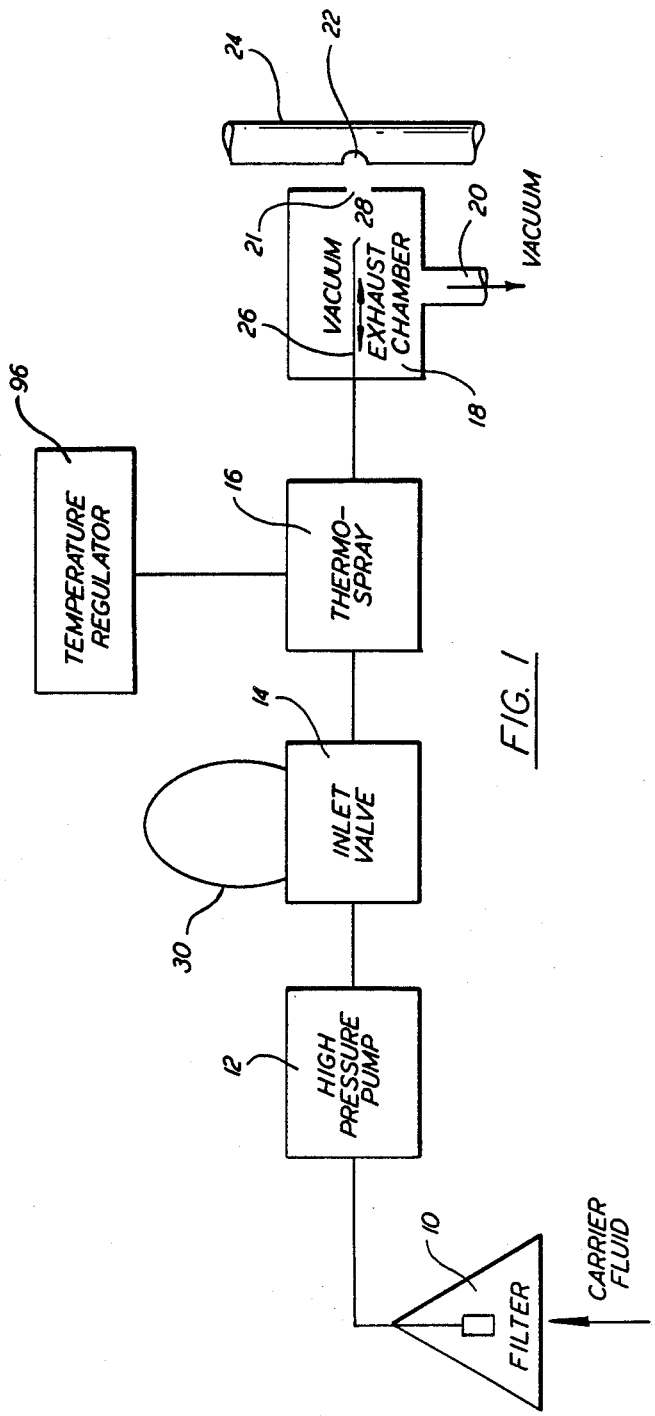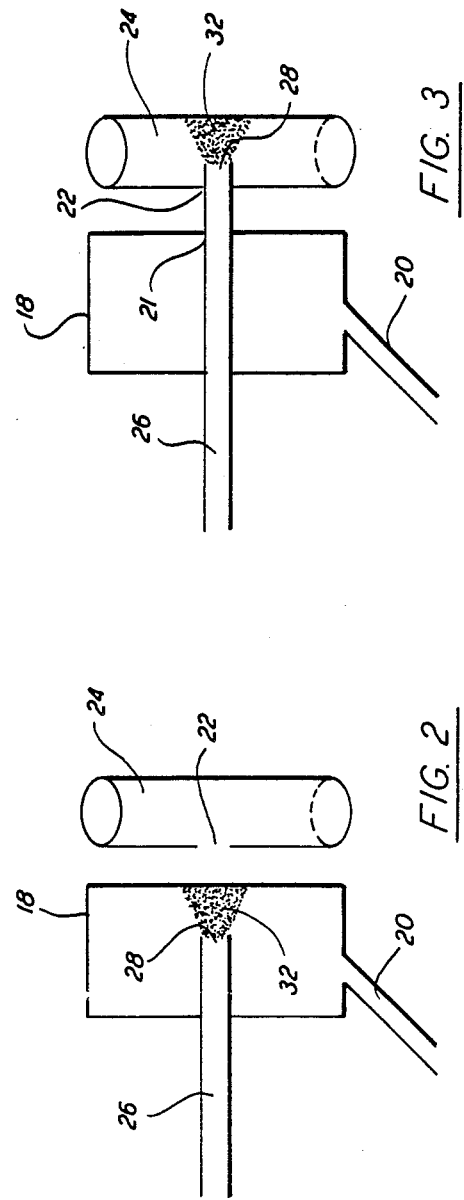

METHOD AND APPARATUS FOR ELECTROTHERMAL ATOMIZATION OF SAMPLES

BACKGROUND OF THE INVENTION

1. Field of the Invention

This invention relates in general to atomic absorption spectrophotometry (AAS) and more particularly to methods and apparatus for electrothermally atomizing a sample in preparation for its qualitative or quantitative analysis by AAS.

2. Description of the Prior Art

As is well known, AAS capitalizes on the fact that an element in its atomic state (i.e., in the form of a cloud of atoms) absorbs radiation of a particular wavelength (or frequency) corresponding to the characteristic wavelength which the element emits when appropriately stimulated. This radiation wavelength (or resonance line) is unique for each element; consequently, when a beam of radiation of the wavelength characteristic of the element sought to be determined ("the analyte") is passed through a sample being analyzed in its atomic state, the degree of absorption is proportional to the concentration of the element in the sample which is thus quantitatively analyzed.

The basic apparatus for AAS comprises a source lamp (a hollow cathode or electrodeless discharge lamp) designed to emit radiation of the desired wavelength; means for atomizing the sample to be analyzed; an optical system for forming a beam of the radiation and directing it from the source and through the atomic cloud; and a detector for measuring the intensity of the beam issuing from the atomized sample. This, of course, is a rudimentary system in the nature of a textual schematic drawing. An actual AAS instrument of modern vintage includes various refinements and additional components, e.g., monochromators, background correction means, mechanical and/or electronic beam modulators, etc.

The present invention is concerned primarily with the means by which the sample is atomized. One of these is a burner into which the sample, in solution, is sprayed by a nebulizer; the other, to which the present invention relates, is an electrothermal atomizer that consists of a container (hereinafter referred to as a furnace) configured to allow through passage of the radiation beam and heated to desired temperatures by an electric current passed through the furnace by means of spaced electrodes in contact therewith.

The most common form of furnace, which will be used for exemplary purposes in this description, is a small, thinwalled tube of pyrolytic or pyrolitically-coated graphite, clamped between annular electrodes engaging the ends of the tube and having a sample introduction port in its sidewall at the midpoint of its length. The radiation beam is directed axially through the tube.

While an electrothermal furnace is the atomizer of choice for many elements for which it has lower detection limits and higher sensitivity than flame, it suffers certain disadvantages: one is with respect to the time required for each analysis owing to the fact that after the sample solution is introduced into the furnace, it must be heated to a first, above-ambient "drying temperature", which effects evaporation of the solvent; this accomplished, the heating current is increased to heat the furnace to a higher, "ashing", temperature, which effects decomposition of the residual sample, and, finally, the tube temperature is still further elevated to the (extremely high) temperature required to render the analyte in atomic form. As pointed out by L. de Galan in "Journal of Analytical Atomic Spectrometry, March 1987, vol. 2, pp. 89–93 (at page 89), the typical cycle time for the analysis takes approximately three minutes per sample (including cooling down time) of which only about ten seconds is devoted to the actual analytical step of atomizing the sample, passing the beam through the atom cloud and detecting beam intensity.

Of the total cycle time, approximately one minute each is devoted to drying and ashing, and one minute to cooling and sample introduction. The disproportionate share of time devoted to drying and ashing is necessary because there is a considerable change in volume during the temperature increases and, therefore, rapid, substantially instantaneous heating to atomization temperature would cause the sample to be flushed out of the furnace.

Other shortcomings of conventional electrothermal atomizers are the limited volume of sample liquid which can be accommodated by the graphite tube and the problems inherent in automation of the sample introduction. Typical of currently available "samplers" is that shown in U.S. Pat. No. 4,111,051. It comprises a carousel having at least one ring of sample cups and an arcuately movable sampling tube, the tip of which is alternately positioned in a sample cup where it picks up a measured quantity of sample liquid and in the sample port of the graphite tube where it discharges the liquid. A rinsing station for the pick-up tube is provided to avoid cross-contamination of successive samples.

Various modifications of this basic design have been proposed to improve techniques and apparatus for electrothermal atomization.

Thus, to minimize matrix interference, Sotera, Cristiano, Conley and Kahn, in a technical paper published in *Analytical Chemistry*, vol. 55, No. 2 (1983) at pages 204–208, using a graphite furnace containing a platform, describe a system in which an aerosol of the sample liquid is sprayed on the platform and/or inner wall of the furnace, using a conventional nebulizer such as commonly used in flame AAS. In the course of the analysis, the furnace can be kept at a temperature higher than ambient (e.g., 400K) enabling a reduction in heating and cooling time required.

A technical paper by Blakeley and Vestal in *Analytical Chemistry*, vol. 55 (1983), pages 750–754, describes the use of a "thermospray" device for introducing the effluent of a liquid chromatograph (LC) into a mass spectrometer (MS) which functions as a detector. The structure includes a stainless steel tube brazed to a copper block which contains, and is heated by, cartridge heaters. The inlet end of the tube is coupled to the outlet of the LC separating column. The liquid effluent from the column, heated as it flows through the SS tube, emerges as a supersonic stream of vapor, normally containing minute droplets or particles. The stream is directed through an ion source of the mass spectrometer and into a vacuum chamber. The MS takes the form of a quadrupole mass filter which, with an ion lens, causes the customary convergence and divergence of the ion beam.

Another application of a thermospray device enabling utilization of a gas chromatography (GC) detector for LC is described by Yang, Fergusson and Vestal in *Analytical Chemistry*, vol. 56, (1984), pages 2558–2561. In the described system, the effluent from an LC is deposited by a thermospray device onto a moving belt which conducts it to a standard GC detector.

A more detailed examination of the properties of aerosols by means of a thermospray device and the application thereof to atomic spectroscopy including plasma AES (atomic emission spectroscopy) is reported by Schwartz and Meyer in *Spectrochimica Acta,* vol. 41 B, No. 12 (1986), pages 1287–1298.

The prior art on the subject includes a paper by Wenrich, Bonitz, Bauer, Niebergal and Dittrich in *Talanta,* vol. 32, No. 11 (1985), pages 1035–1039, relating to the introduction of an aerosol sample into a graphite tube furnace by means of an ultrasonic atomizer. According to this publication, either the furnace is operated at a constant temperature and sample liquid continuously introduced in the form of an aerosol or the sample can be deposited on the inner wall of the graphite tube and the furnace heated discontinuously. To avoid overloading the furnace and the formation of hydrogen, the sample solvent is vaporized and drawn off in an evaporating unit connected upstream of the furnace.

An electrothermal sample atomization system for AAS providing pre-vaporization of the solvent and having discontinuous heating of the furnace is described by Kantor, Clyburn and Veillon in *Analytical Chemistry,* vol. 46, No. 14 (1974), pages 2205–2215.

SUMMARY OF THE INVENTION

With the foregoing state of the art in view, it is the general objective of the present invention to overcome or at least mitigate the shortcomings and disadvantageous aspects of currently available methods and apparatus for sample introduction in AAS.

More specific objects are the reduction in cycle time for each analysis performed; the accommodation of larger samples than with known methods and apparatus; and the provision of sample introduction methods and apparatus for sample introduction which lend themselves to simple automation.

For the accomplishment of the foregoing and other objectives which will become apparent as this description proceeds, the invention contemplates a method for electrothermal atomization of samples for analysis by atomic absorption spectrophotometry in which the furnace is heated to a first above-ambient temperature, the furnace being tubular in configuration or otherwise shaped to receive a sample and to accommodate transmission of a radiation beam of a pre-selected wavelength. The sample, in liquid form, is sufficiently heated in a capillary tube to cause at least a major fraction thereof to vaporize. One end of the capillary tube is intermittently inserted into the furnace and a jet of vaporized sample injected into the furnace so as to impinge on an inner surface of the furnace. The furnace then is heated to a temperature higher than said first temperature and sufficient to atomize the sample. A beam of radiation then is passed through the sample and the degree of absorption thereof by the sample measured. The furnace is then allowed to cool down.

The invention also contemplates an apparatus for electrothermal atomization of samples for analysis by atomic absorption spectrophotometry which comprises a furnace normally heated to the above-ambient temperature and shaped to permit passage therethrough of a substantially monochromatic radiation beam of a pre-selected wavelength, the furnace having a sample introduction port and means for introduction of a sample through the port and deposition thereof on an inner surface of the furnace.

The sample introduction means includes a heated capillary tube through which the liquid sample passes and at least a major portion thereof is caused to be vaporized. The tube has an outlet end adapted to inject the vaporized sample through the port into the furnace. The heated capillary tube is mounted for axial displacement between a first retracted position in which the outlet end is withdrawn from the sample port and a second sample introduction position in which the outlet end extends through the sample port into the furnace. Means are provided for moving the tube between the first and second positions. A vacuum exhaust chamber is so arranged that the outlet end of the capillary tube is disposed therein when in the retracted position. The inlet end of the capillary tube is adapted for flow communication with a source of pressurized carrier liquid thus to provide a stream of such carrier liquid to the capillary tube. An inlet valve having a sample loop is connected in the flow path of the carrier liquid upstream of the heated capillary tube. A displaceable shutter member is interposed between the furnace and the vacuum exhaust chamber and selectively operable means are provided to move the shutter to and from positions in which it occludes communication between the exhaust chamber and the furnace. The capillary tube is made of fused silica and is coaxially surrounded by a stainless steel tube, the ends of which are adapted for connection to electrical contacts for passing electric current therethrough.

Additional objects and advantages of the invention, its scope and the manner in which it may be practiced will be more readily apparent to those conversant with the art from the following description and subjoined claims taken in conjunction with the annexed drawings wherein like reference characters designate like parts throughout the several views.

BRIEF DESCRIPTION OF DRAWINGS

FIG. 1 is a block diagram of an apparatus for electrothermal atomization of a sample for analysis by atomic absorption spectrophotometry in accordance with the present invention;

FIG. 2 is a fragmentary schematic view showing the forward end of the capillary tube in its retracted position;

FIG. 3 is a schematic fragmentary view identical to FIG. 2 except that the capillary tube of the thermospray device is in its forward or sample introduction position, the outlet end projecting through the sample port of the furnace;

FIG. 6b is a perspective view of the furnace tube removed from, but showing its general spatial relation to, the remainder of the apparatus shown in FIG. 6a;

Figure 4:
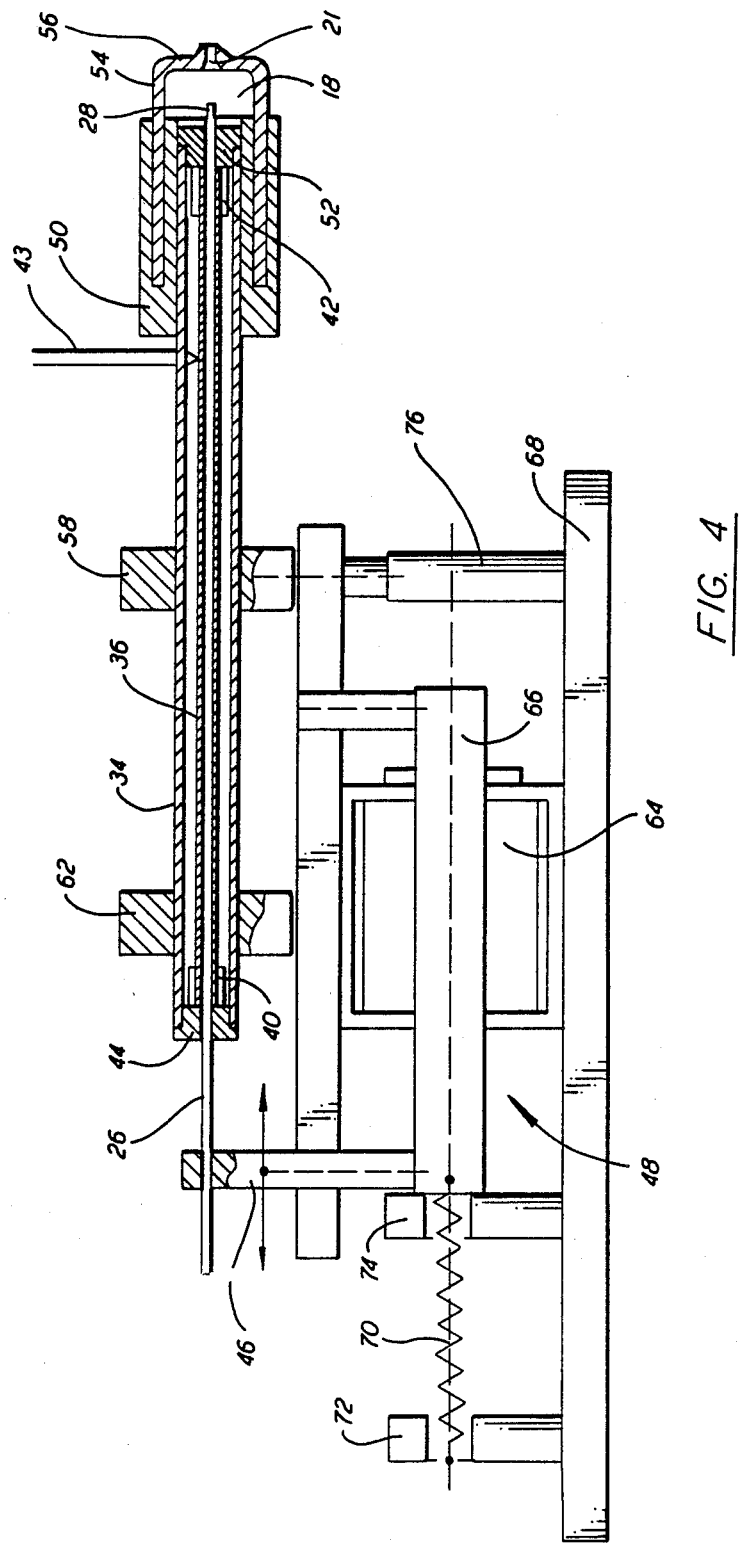
FIG. 4 is an elevational view partially in axial section through the capillary tube of the thermospray device shown in its retracted position relative to the furnace.

Referring to the drawings and first in particular to FIG. 1, numeral 10 designates a filtered source of deionized water or other carrier liquid which is supplied by a high pressure pump 12 to an inlet valve 14 of a thermospray device 16. As will be described presently in greater detail, thermospray device 16 comprises a capillary tube 26 mounted for axial displacement between a forward sample introduction position and a retracted position. In the forward position, the outlet end 28 of capillary tube 26 extends through an aperture 21 in a vacuum exhaust chamber 18 and into a sample introduction port 22 in a graphite furnace tube 24 adjacent the chamber, the aperture and port being coaxially aligned.

In the retracted position (as shown in FIG. 1), outlet end 28 of tube 26 is disposed in exhaust chamber 18. A vacuum is maintained in chamber 18 by means of a conduit 20 leading to a vacuum exhaust line, a vacuum pump or other source of sub-ambient pressure (not shown).

Furnace 24 is a conventional graphite tube heated by means of an electrical current passed longitudinally through the tube between annular electrode members (not shown in FIG. 1) engaging the tube ends.

Inlet valve 14, upstream of thermospray device 16, is equipped with a sample loop 30 which can selectively be coupled into, or by-passed by, the flow stream of carrier liquid. When the capillary tube 26 is in its advanced position and sample loop 30 is coupled into the flow stream, a jet of completely or almost completely vaporized sample is deposited on the inner wall of furnace tube 24.

This process is schematically depicted in FIGS. 2 and 3. In FIG. 2, capillary tube 26 is shown in its retracted position wherein its end 28 is disposed in vacuum exhaust chamber 18. A jet of totally or almost entirely vaporized carrier liquid issues into chamber 18 and is exhausted through outlet conduit 20.

In FIG. 3, capillary tube 26 is advanced so that its free end 28 projects through aperture 21 and sample port 22 into the interior of graphite furnace tube 24 where it impinges on the inner wall. The furnace is pre-heated to drying temperature, e.g., 200° C.; consequently, the sample component(s) being determined deposit on the furnace wall while the vaporized carrier is flushed from the tube by the inert protective gas which conventionally is passed through the furnace to prevent its combustion at the high temperatures required for atomization.

When introduction of the sample has been accomplished in this manner, capillary tube 26 is withdrawn to its retracted position (FIG. 2) and aperture 21 is closed, as will be described presently, in order to enable efficient exhaustion of the vaporized carrier liquid from chamber 18.

The structural implementation of the invention will now be described with continued reference to FIGS. 4, 5, 6a and 6b.

As best appears in FIG. 4, thermospray device 16 comprises the capillary tube 26, preferably made of fused silica and is slidably encased in a coaxial stainless steel (SS) tube 36 over a major portion of its length. At its free end 28, the tip of capillary 26 projects from tube 36 and at its opposite end it projects a considerably greater distance and is connected to a pin 46 and is in flow communication with inlet valve 14.

In one practical embodiment, capillary 26 has an internal diameter (I.D.) of 300 micrometers; SS tube 36 has an I.D. of 500 micrometers and is about 20 cm. in length.

At its ends SS tube 36 is connected by electric contacts 40, 42 to a source of electric power (not shown) and is heated by passage of an electric current therethrough. The temperature of tube 36 is indicated by Chromel-Alumel thermocouples in proximity to its ends, one of which is shown at 43.

Tube 36 is coaxially mounted within a tubular housing 34 by means of bushings 44 and 52 which close the respective ends of the housing.

A cylindrical end member 50 mounts a cup-shaped end cap 56 on the front end (the right hand end as viewed in FIG. 4) of tubular housing 34. End cap 56 coacts with bushing 52 to form the vacuum exhaust chamber 18, previously described, and defines the opening 21, also previously described, in end wall 56 through which the sample vapor jet is directed into graphite furnace tube 24. Opening 21 has a cone-shaped inner wall, tapering outwardly in the direction of bushing 52 to facilitate entry of the free end 28 of capillary tube 26 when moved to its forward, sample injection position, where it closes the opening.

Figure 5:
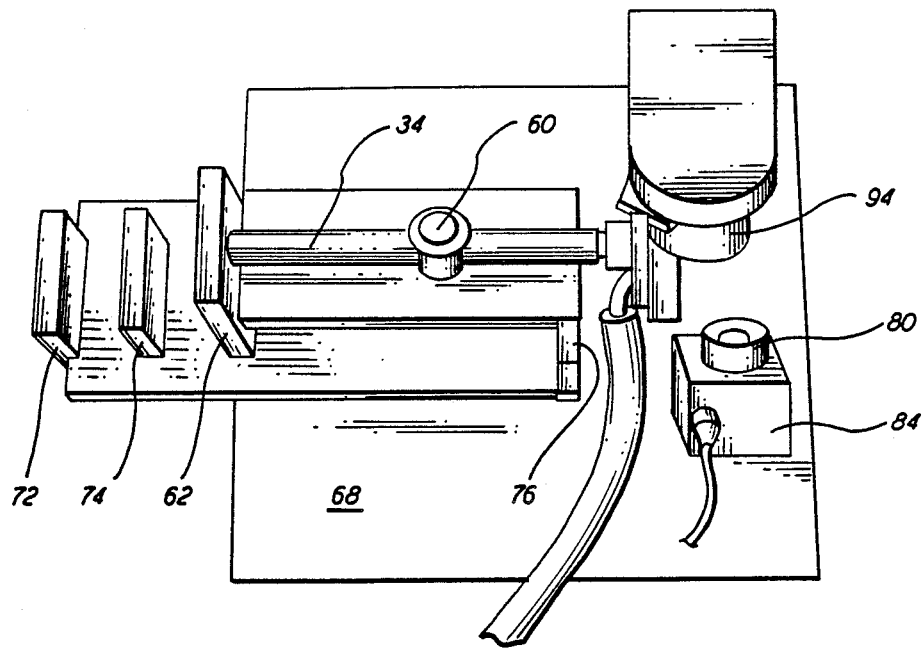
FIG. 5 is a simplified perspective view of apparatus embodying a system of FIG. 1 as viewed at an angle from above.
Figure 6A:
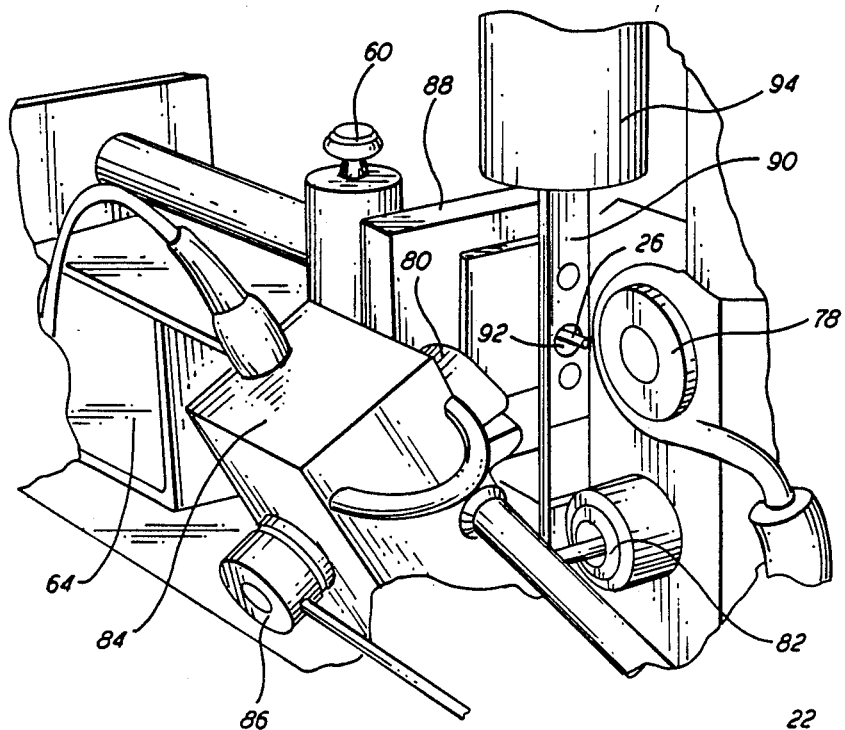
FIG. 6a is a perspective view similar to FIG. 5 but showing the apparatus as viewed from the furnace end; the furnace being removed.

As shown in FIGS. 4, 5 and 6a, tubular housing member 34 is mounted in spaced, forward and rear supports 58 and 62, respectively; the supports contain aligned bores receiving the tubular housing and accommodating axial adjustment of the housing. A knurled screw locks housing 34 in axially adjusted position.

A servomotor 48 is operable to displace capillary tube 26 between its forward and retracted positions. To this end, the solenoid 64 of servomotor 48 is mounted on a base plate 68 and has its armature 66 biased to the left as viewed in FIG. 4 by means of a tension spring 70. One end of spring 70 is fastened to armature 66 and the other end is anchored to a stop member 74 mounted on base plate 68. Thus, armature 66 is normally held against stop member 74, which defines the retracted position of capillary tube 26, by the action of tension spring 70.

Figure 6B:
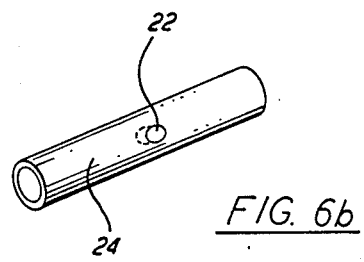

Referring to FIG. 6a, there is shown in perspective view the overall electrothermal atomizer structure with the furnace tube 24 removed and shown separately in FIG. 6b. When installed in the atomizer, tube 24 has its ends clamped between annular graphite electrodes 78 and 80. Electrode 78 is fixedly mounted with respect to the base plate 68 whereas electrode 80 is part of a subassembly 84 pivotally mounted to permit insertion and removal of the furnace tubes. The subassembly 84, which contains a window 86 and cooling chambers, is shown in its open position, i.e., tilted away from the stationary main assembly. Movement of subassembly 84 between open and closed positions is effected by means of a pneumatic servomotor 82. A graphite tube furnace is described in greater detail in U.S. Pat. No. 4,176,956.

A partition or dividing wall 88 separates thermospray device 16 from the graphite furnace proper. Partition 88 contains an aperture not visible in FIG. 6a which can be occluded by a shutter member 90 which also contains an aperture 92 aligned with that in partition 88 in one shutter position. In a second position, the apertures in the shutter member and the partition 88 are out of registration, thus closing the aperture corresponding to opening 21, in FIG. 4. Shutter member 90 is moved between the first and second positions by means of a servomotor 94. When in the first position, the tip 28 of capillary tube 26 protrudes through aperture 92 and into sample port 22 of furnace tube 26 as schematically illustrated in FIG. 3.

Reverting to FIG. 1, a temperature controller 96 regulates the temperature of stainless steel tube 36 and, concomitantly, capillary tube 26.

Figure 7:
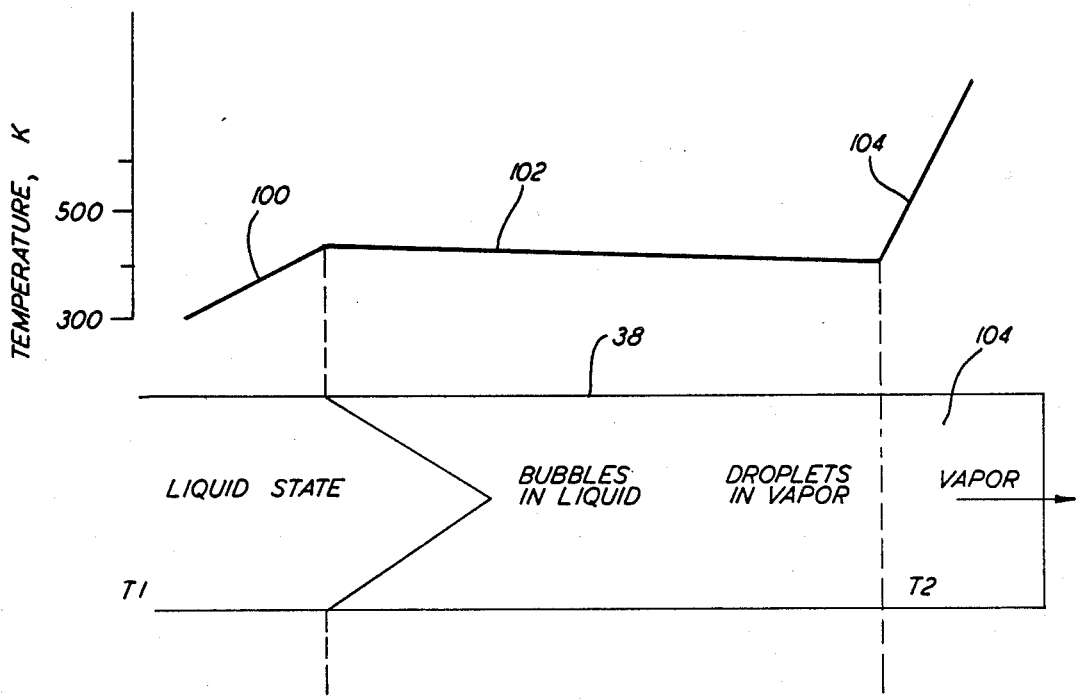
FIG. 7 is a graphic representation of the progression of temperature and condition (physical state) of the sample along the length of the thermospray device.

The above-described embodiment of the invention operates in the following manner. In the rest position, which is illustrated in FIGS. 1, 2 and 4, i.e., with capillary tube 26 retracted, the outlet end 28 of the tube is located within vacuum exhaust chamber 18. Sample loop 30, albeit filled with a sample liquid, is maintained outside the flow path of the carrier liquid by inlet valve which establishes a direct connection between high pressure pump 12 and thermospray device 16. At least a predominant portion of the carrier liquid is vaporized in thermospray 16. The advance of temperature along the length of capillary tube 28 within stainless steel tube 36 is graphically illustrated in FIG. 7 to which reference is now made.

At the inlet (left hand) side of the flow path, liquid is flowing into the capillary under the impetus of high pressure pump 12. The liquid is progressively heated in accordance with its heat capacity resulting in a linear increase in temperature as indicated by the linear slope of line 100. As the liquid vaporizes, consumption of the heat of vaporization prevents any further temperature increase as represented by horizontal line segment 102. As the liquid passes through capillary 26 in the constant temperature region, bubbles are formed beginning at first with liquid in proximity to the wall of the tube and progressing inwardly toward the center line of the fluid stream. Further along toward the outlet end, the liquid turns into droplets which are carried along in a vapor stream. With increasing vaporization, the volume of the liquid increases markedly causing a corresponding increase in flow velocity. In the final region 104, liquid is completely vaporized and a steep increase in temperature takes place, as there is no longer need for heat of evaporization and the Joule effect heats only the relatively small heat capacity of the vapor. Consequently, at the outlet end of capillary 26, vaporized liquid issues at a high rate of flow.

Thus, in the rest position initially the vaporized carrier liquid, viz., water vapor, issues from the capillary tube. As the end of the tube is in the vacuum exhaust chamber, the water vapor is drawn off through port 20. Furnace 24 is heated to a drying temperature appropriate to the sample, e.g., 200° C. and is maintained at this temperature throughout the rest condition.

To initiate the analysis, capillary 26 is advanced by servomotor 48 to its sample introduction position so that the tip 28 of tube 26 extends through opening 21 and sample inlet port 22 of the furnace 24 as illustrated in FIG. 3. Contemporaneously, inlet valve 14 connects sample loop 30 into the flow path of the carrier liquid. The carrier liquid flows through sample loop 30 and thus transports the sample liquid through capillary tube 26 of the thermospray device. During its passage through the capillary tube, the sample liquid, and particularly the solvent portion thereof, is vaporized. The vaporized sample liquid impinges on the inner wall of furnace tube 24 preheated to the drying temperature. At this juncture, the sample substances to be determined are not yet volatile and consequently are deposited on the inner furnace wall. Vaporized solvent, on the other hand, is flushed out of the furnace tube by the customary inert gas flow utilized to prevent combustion of the graphite at the high temperature required for atomization. It will be appreciated that the amount of sample deposited constitutes a small proportion of the initial sample liquid. Consequently, a considerably larger quantity of sample liquid can be employed than with known electrothermal atomization techniques wherein the sample liquid is introduced in the form of drops applied directly into the cold furnace tube.

In a preferred form of the method, a 10 microliter quantity of sample material is introduced into furnace tube 24 together with an additional 40 to 60 microliters of water or other solvent. The additional water is for the purpose of rinsing capillary tube 26 and sample loop 30. With a flow rate of 1 ml per minute, about 3 to 4 seconds is required for deposition of the sample on the inner wall of furnace tube 24.

After deposition of the sample in the furnace tube, shutter member 90 is moved by servomotor 94 into its second position, in which the aperture in partition 88 is covered. Then furnace tube 24 is heated to the appropriate atomization temperature. The deposited sample is atomized and a "cloud of atoms" is formed in the furnace tube. The spectral radiation beam directed through furnace tube 24 is absorbed in proportion with the concentration of the element being determined in the sample. This is the conventional technique employed for analysis using atomic absorption spectroscopy. Shutter member 90 shields furnace tube 24 from opening 21 of the vacuum exhaust chamber 18, thus ensuring that no water vapor can reach the furnace during atomization when the furnace is heated to a high temperature. Exposure of the graphite tube to water vapor at atomizing temperatures could cause damage to the tube.

Figure 8:
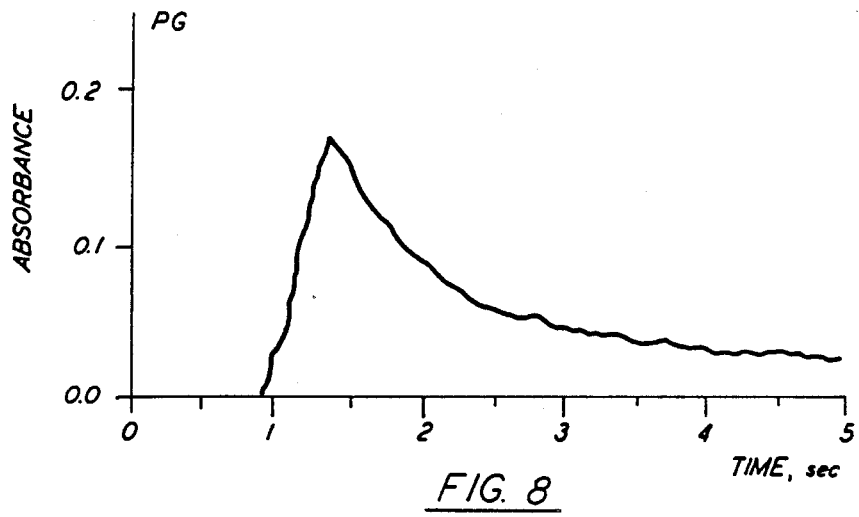
FIG. 8 is a plot of absorbance against time showing the signal waveform obtained with electrothermal atomization of a vanadium sample according to the present invention.

FIG. 8 is a graph of the absorption signal (absorbance versus time) which was obtained using this method with a sample of 2 ng vanadium in a 200 ppb solution. The shape of the signal plot resembles that obtained with conventional sample introduction, i.e., introducing a drop of sample liquid into the cold furnace tube. Furnace tube 24 was maintained at a drying temperature of 200° C. The temperature of thermospray device 16 was 320° C. This resulted in an efficiency of 60% as compared to conventional sample introduction.

Figure 9:
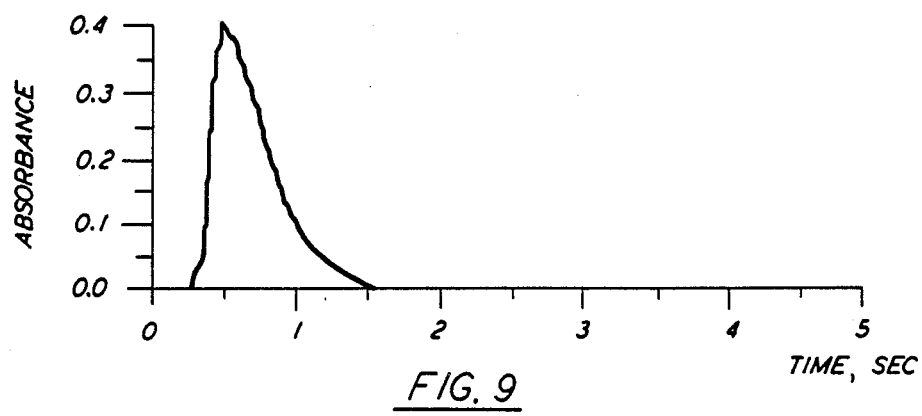
FIG. 9 is a plot of absorbance against time showing the signal waveform obtained with electrothermal atomization of a silver sample according to the present invention.

FIG. 9 is a graph of the absorption signal comparable to FIG. 8 for 0.2 ng silver in a 20 ppb silver solution using the same temperature conditions as employed for the vanadium sample. As in the first example, the shape of the absorption signal resembles that obtained with conventional sampling methods. The resulting efficiency was 65%.

Figure 10:
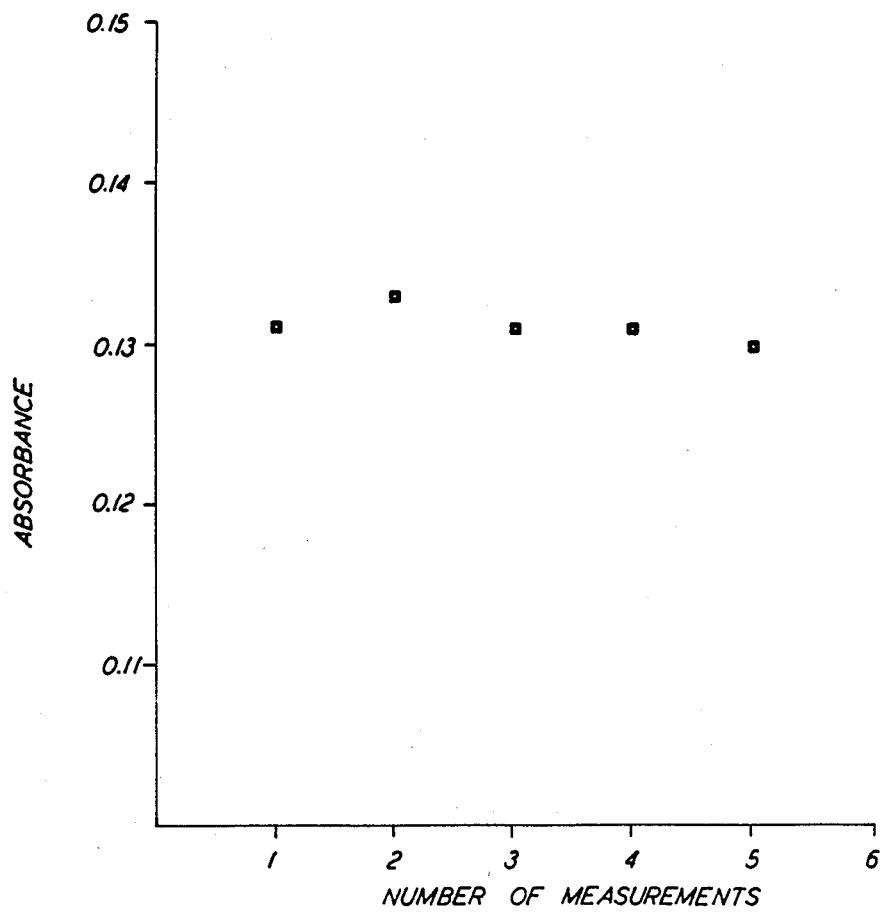
FIG. 10 is a graphic representation illustrating the consistency of the absorbance values for five measurements of a single sample atomized in accordance with the present invention.

FIG. 10 illustrates the consistency or repeatability of the analytical measurements. Identical samples (five in number) of a 200 ppb vanadium solution were successively analyzed with a drying temperature of 200° C. and a thermospray temperature of 335° C. This resulted in a standard deviation of 0.84% which value is comparable with values obtained using a conventional "autosampler" for sample introduction (into a cold furnace tube).

Figure 11:
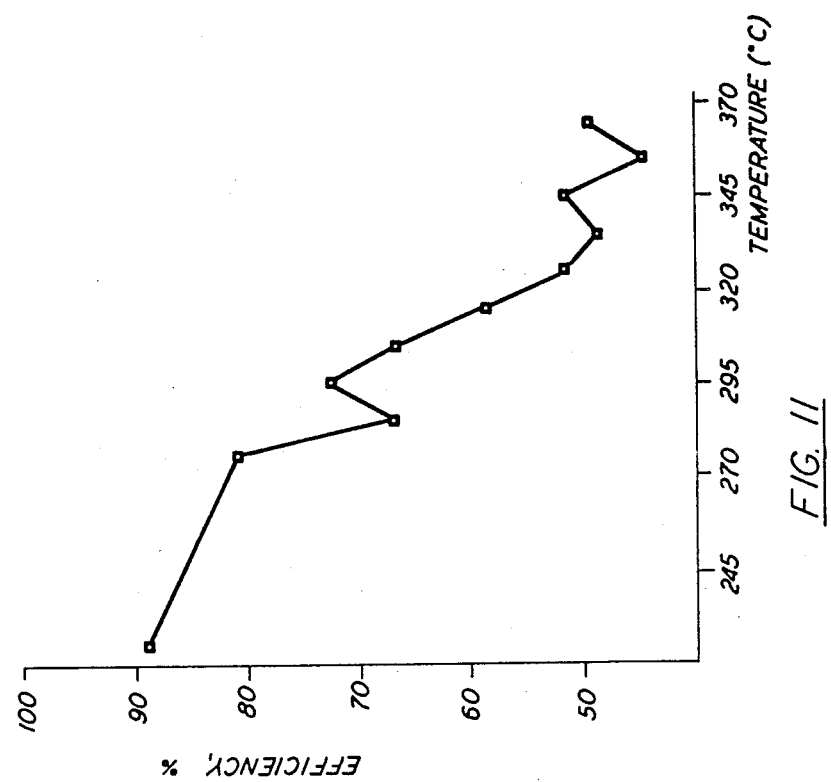
FIG. 11 is a graph showing the dependence of efficiency with electrothermal atomization as compared to conventional sample introduction as a function of the temperature of the thermospray device.

FIG. 11 graphically illustrates the dependency of the efficiency (as compared to conventional sample introduction viz., a drop of sample liquid directly into the unheated furnace tube) on the temperature of thermospray device 16. With the furnace tube at a constant drying temperature of 200° C., a 200 ppb vanadium solution was analyzed while the temperature of the thermospray device was adjusted to setpoints between 225° C. and 365° C. The I.D. of capillary tube 26 was 100 micrometers and the flow rate 0.7 ml per minute. It was found that the efficiency is reduced from about 90% to 50% with increasing thermospray device temperatures.

Figure 12:
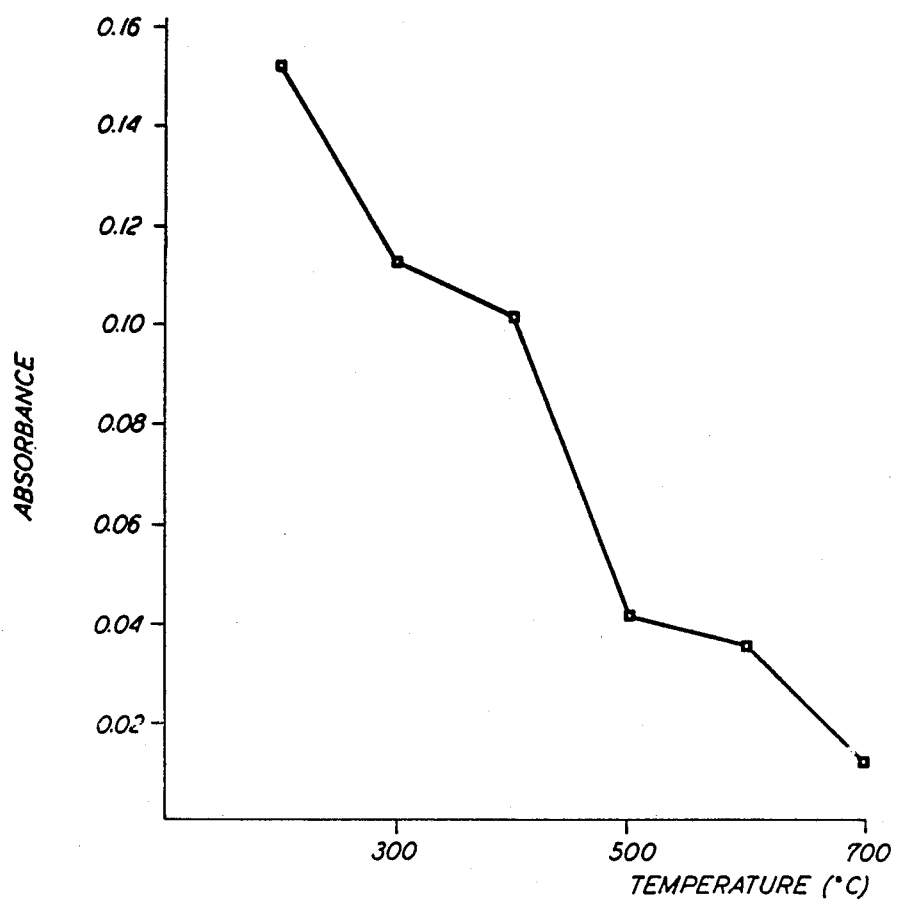
FIG. 12 is a graph showing the dependence of efficiency with electrothermal atomization as compared to conventional sample introduction as a function of the drying temperature of the furnace, i.e., the temperature of the furnace when the sample is deposited on the inner wall of the furnace.

FIG. 12 graphically presents the absorbance obtained with identical samples at different drying temperatures of furnace tube 24 and at a constant temperature of the thermospray device. As in the previous example, a 10 microliter sample of a 200 ppb vanadium solution was used. The temperature of the thermospray device 16 was maintained constant while the temperature of furnace tube 24 was varied from 200° to 700° C. The absorbance dropped from 0.16 to 0.02 with increasing temperature.

Figure 13:
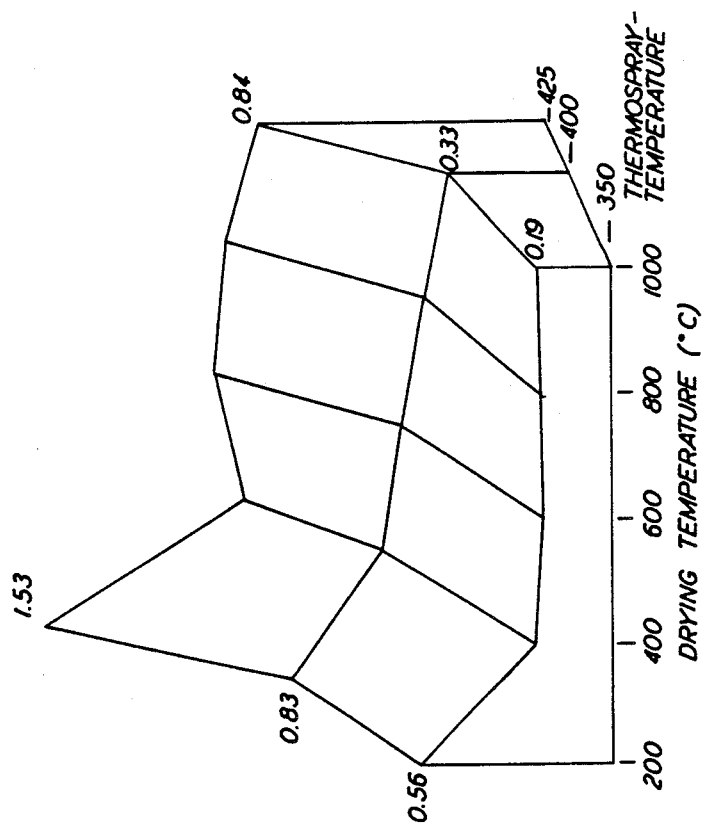
FIG. 13 is a three-dimensional graphic presentation showing the absorbance signal of a silver sample as a function of both the temperature of the thermospray device and of the drying temperature of the furnace.

FIG. 13 is a three-dimensional graph of absorbance signal (in the form of peak heights) as a function of drying temperature of furnace tube 24 and the temperature of thermospray device 16. Absorbance measurements were made with a 10 microliter sample of a 100 ppb silver solution. The highest efficiency for Ag was obtained when the drying temperature of furnace tube 24 was low and the temperature of thermospray device 16 was high.

The contrast between results obtained for V (FIGS. 11 and 12) and Ag (FIG. 13) demonstrate the need to optimize temperatures. A low drying temperature increases the efficiency because the sample substances deposit more readily on a relatively cold inner wall of furnace tube 24. However, the drying temperature naturally must be sufficiently high that the solvent remains in its vapor state. It is also understandable that a reduction in efficiency for V accompanies increased thermospray device temperature by increasing the outlet speed of the sample vapor issuing from capillary tube 26.

Figure 14:
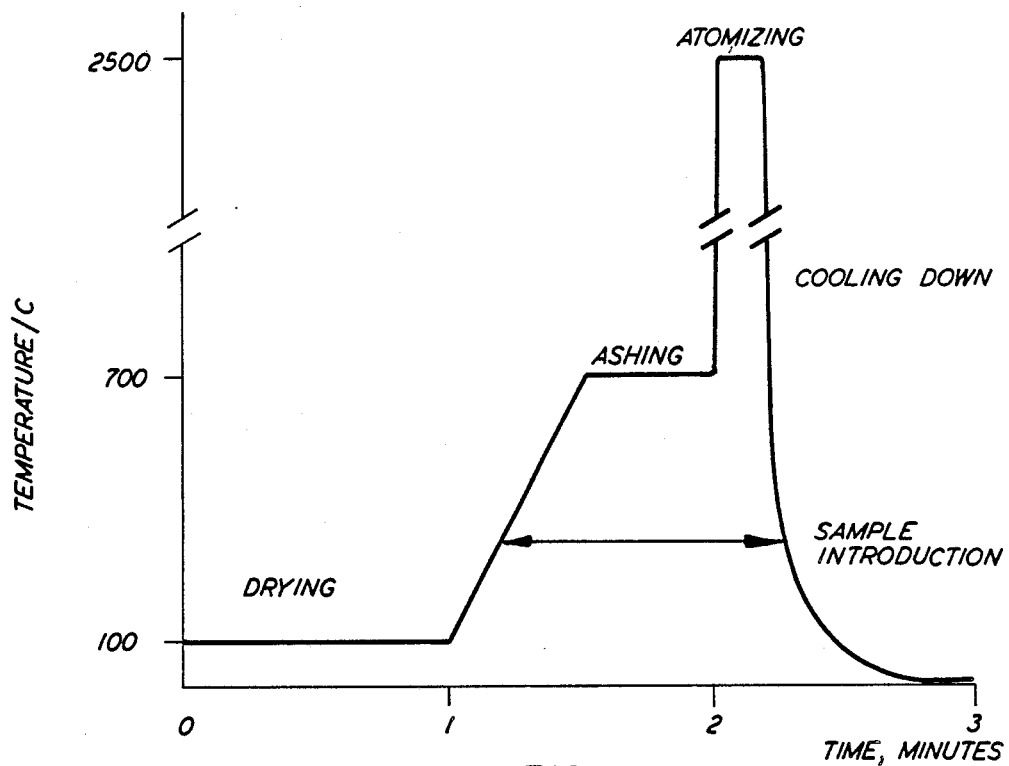
FIG. 14 is a plot of the progression of temperature of the furnace against time with a conventional electrothermal atomizer.

FIG. 14 shows the temperature cycle of a furnace tube with conventional sample introduction, viz., drops of liquid sample deposited in a cold furnace tube. It will be noted that about one minute of the total analysis time is required to dry the sample, i.e., to evaporate the solvent. Approximately one additional minute is required for ashing the sample and still another minute for the furnace to cool down substantially to ambient temperature. A very brief period of time, in the order of seconds, is required for atomization and actual absorbance measurement. As has already been pointed out, total analysis time is reduced markedly by starting at an elevated temperature instead of room temperature as shown in FIG. 14.

Figure 15:
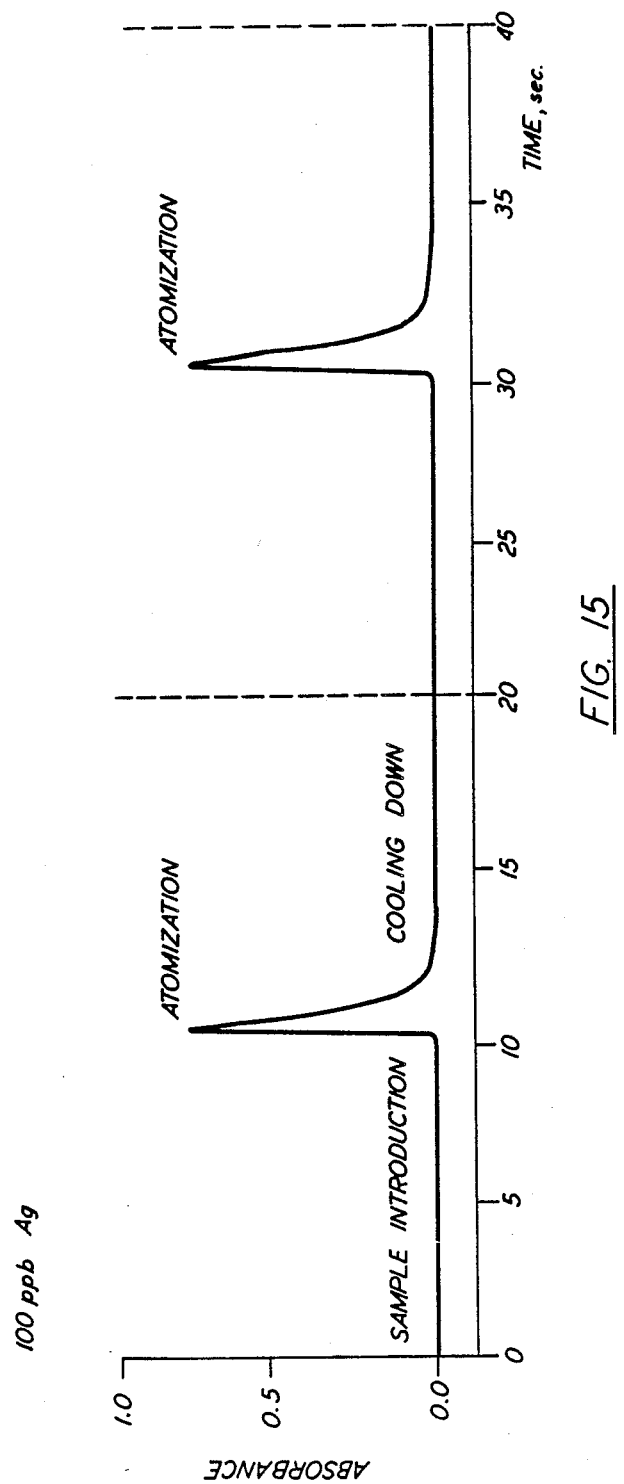
FIG. 15 is a graphic presentation of absorbance versus time showing the cycle time of a sample analysis utilizing atomization according to the present invention.

For purposes of comparison, FIG. 15 shows the process as a function of time in an analysis in accordance with the above-described method. The absorbance measured in atomic absorption spectroscopy with successive samples is plotted as a function of time. It can be seen that the time durations for the sample preparation to the atomization and for the cooling down of the furnace are in the order of 10 seconds, so that the total analysis cycle consumes only about 20 seconds.

Therefore, the described method enables a significant reduction in the time required for the electrothermal atomization and consequently in the time required for the complete analysis cycle. While this may be achieved at the cost of lowered efficiency as compared to direct introduction of sample liquid into the furnace, this is more than compensated by the fact that larger quantities of sample liquid can be processed in each measurement. The overall result is an increase of sensitivity. Finally, atomization of sample introduction can be carried out with commercially available components.

While there have been described what at present are believed to be the preferred embodiments of this invention, it will be obvious to those skilled in the art that various changes and modifications may be made therein without departing from the invention, and it is aimed, therefore, to cover in the appended claims all such changes and modifications as fall within the true spirit and scope of the invention.

What is claimed is:

1. A method for electrothermal atomization of samples for analysis by atomic absorption spectrophotometry comprising the steps of:
   (a) heating to a first, above-ambient temperature a furnace shaped to receive a sample and to accommodate transmission of a radiation beam of preselected wavelength;
   (b) heating a liquid sample in a capillary tube to cause at least a major portion thereof to vaporize;
   (c) intermittently inserting one end of the tube into said furnace and forming a jet of the vaporized sample injected into the furnace so as to impinge on an inner surface thereof;
   (d) heating the furnace to a temperature higher than said first temperature and sufficient to atomize the sample;
   (e) passing a beam of radiation through the atomized sample and measuring the degree of absorption thereof by the sample; and
   (f) allowing the furnace to cool down to said first temperature.

2. A method according to claim 1, including the further steps of
   (a) withdrawing said one end of the tube from the furnace during time intervals interspersed between injections of the sample;
   (b) pumping a carrier liquid through the tube toward said one end while withdrawn from the furnace; and (c) subjecting said one end of the tube to a vacuum while withdrawn from the furnace.

3. A method according to claim 2 wherein sample liquid is introduced into the flow path of said carrier liquid upstream of the other end of said capillary tube.

4. A method according to claim 3 wherein a barrier is moved into place between said one end of the capillary tube and the furnace after withdrawal from the furnace.

5. Apparatus for electrothermal atomization of samples for analysis by atomic absorption spectrophotometry, comprising:
   (a) a furnace normally heated to an above-ambient temperature and shaped to permit passage therethrough of a substantially monochromatic radiation beam of a selected wavelength, said furnace having a sample introduction port; and
   (b) means for introduction of a liquid sample through said port and deposition thereof on an inner surface of said furnace, said means including a heated capillary tube, through which said sample passes and in which at least a major portion thereof is vaporized, the tube having an outlet end adapted to inject the vaporized sample through said port into the furnace.

6. Apparatus according to claim 5 including means for mounting said heated capillary tube for axial displacement between a first retracted position in which said outlet end is withdrawn from said sample port and a second, sample introduction position in which said outlet end extends through the sample port into the furnace; and
   means for moving said tube between said first and second positions.

7. Apparatus according to claim 6 further including means defining a vacuum exhaust chamber so arranged that the outlet end of said capillary tube is disposed therein when in said retracted position.

8. Apparatus according to claim 7 wherein the inlet end of the capillary tube is adapted for flow connection to a source of pressurized carrier liquid and thus to provide a stream of such carrier liquid through said capillary tube; and
   an inlet valve having a sample loop is connected in the flow path of the carrier liquid upstream of the heated capillary tube.

9. Apparatus according to claim 8 further including means defining a displaceable shield interposed between said furnace and exhaust chamber; and means selectively operable to move said shield to and from positions in which it occludes communication between said exhaust chamber and said furnace.

10. Apparatus according to claim 9, wherein said capillary tube is made of fused silica and said apparatus includes a stainless steel tube coaxially surrounding said capillary tube, the ends of said steel tube being adapted for connection to electric contacts for passing an electric current therethrough for directly heating same.

* * * * *